US012758088B2

(12) United States Patent
Yangdai

(10) Patent No.: US 12,758,088 B2
(45) Date of Patent: Oct. 13, 2026

(54) COMPLETENESS SELF-CHECKING METHOD OF CAPSULE ENDOSCOPE, ELECTRONIC DEVICE, AND READABLE STORAGE MEDIUM

(71) Applicants: ANKON TECHNOLOGIES CO., LTD, Wuhan (CN); ANX IP HOLDING PTE. LTD., Singapore (SG)

(72) Inventor: Tianyi Yangdai, Wuhan (CN)

(73) Assignees: ANKON TECHNOLOGIES CO., LTD, Wuhan (CN); ANX IP HOLDING PTE. LTD., Singapore (SG)

( * ) Notice: Subject to any disclaimer, the term of this patent is extended or adjusted under 35 U.S.C. 154(b) by 419 days.

(21) Appl. No.: 18/551,190

(22) PCT Filed: Mar. 10, 2022

(86) PCT No.: PCT/CN2022/080075
§ 371 (c)(1),
(2) Date: Sep. 18, 2023

(87) PCT Pub. No.: WO2022/194014
PCT Pub. Date: Sep. 22, 2022

(65) Prior Publication Data

US 2024/0164627 A1 May 23, 2024

(30) Foreign Application Priority Data

Mar. 17, 2021 (CN) ........................ 202110285332.9

(51) Int. Cl.
*A61B 1/04* (2006.01)
*A61B 1/00* (2006.01)

(52) U.S. Cl.
CPC .......... *A61B 1/041* (2013.01); *A61B 1/00006* (2013.01); *A61B 1/00057* (2013.01)

(58) Field of Classification Search
CPC . A61B 1/041; A61B 1/00006; A61B 1/00057; A61B 1/009; A61B 1/0058;
(Continued)

(56) References Cited

U.S. PATENT DOCUMENTS

2008/0117210 A1 5/2008 Barcon
2014/0180063 A1* 6/2014 Zhao ........................ G06T 7/75 600/424

(Continued)

FOREIGN PATENT DOCUMENTS

CN 109907720 A 6/2019
CN 110136808 A 8/2019

(Continued)

*Primary Examiner* — Ryan N Henderson
*Assistant Examiner* — Pamela F Wu
(74) *Attorney, Agent, or Firm* — Treasure IP Group, LLC

(57) ABSTRACT

The present invention provides a completeness self-checking method of a capsule endoscope, an electronic device, and a readable storage medium. The method comprises: driving the capsule endoscope to move within a working area and capturing images upon reaching each working point, and synchronously executing a step A; the step A comprises: recording the position and field of view orientation of each working point; determining an intersection area between the field of view of the capsule endoscope and a virtual positioning area; obtaining each voxel that is not labeled with illuminated identifier in each intersection area, and obtaining a line of sight vector from the current working point to each voxel that is not labeled with illuminated identifier, and merging the line of sight vectors into the same vector set; labeling the voxels corresponding to the current (Continued)

vector set with illuminated identifiers. It implements the completeness self-checking of the capsule endoscope.

10 Claims, 3 Drawing Sheets

(58) Field of Classification Search
CPC . A61B 1/008; A61B 34/20; A61B 2034/2046; A61B 2034/2051
USPC .......................................... 600/101, 160, 112
See application file for complete search history.

(56) References Cited

U.S. PATENT DOCUMENTS

| | | | | |
|---|---|---|---|---|
| 2014/0336501 | A1* | 11/2014 | Masumoto | A61B 1/31 600/417 |
| 2018/0235709 | A1* | 8/2018 | Donhowe | A61B 34/35 |
| 2019/0388123 | A1* | 12/2019 | Pavlovskaia | G06T 19/00 |
| 2021/0192759 | A1* | 6/2021 | Lang | A61B 90/37 |

FOREIGN PATENT DOCUMENTS

| | | | |
|---|---|---|---|
| CN | 111932532 | B | 1/2021 |
| WO | 2012163779 | A1 | 12/2012 |

* cited by examiner

COMPLETENESS SELF-CHECKING METHOD OF CAPSULE ENDOSCOPE, ELECTRONIC DEVICE, AND READABLE STORAGE MEDIUM

CROSS-REFERENCE OF RELATED APPLICATIONS

The application is a National Phase Application of PCT International Application No. PCT/CN2022/080075, International Filing Date Mar. 10, 2022, published Sep. 22, 2022 as International Publication Number WO2022/194014A1, which claims priority from Chinese Patent Application No. 202110285332.9, filed Mar. 17, 2021, all of which are incorporated herein by reference in their entireties.

FIELD OF INVENTION

The present invention relates to the field of medical devices, and more particularly to a completeness self-checking method of a capsule endoscope, an electronic device, and a readable storage medium.

BACKGROUND

Capsule endoscopes are increasingly used for gastrointestinal examinations. A capsule endoscope is ingested and passes through the oral cavity, esophagus, stomach, small intestine, large intestine, and is ultimately expelled from the body. Typically, the capsule endoscope moves passively along with gastrointestinal peristalsis, capturing images at a certain frame rate during this process. The captured images are then used by a physician to assess the health condition of various regions of a patient's gastrointestinal tract.

Compared to traditional endoscopes, the capsule endoscope offers advantages such as no cross-infection, non-invasiveness, and high patient tolerance. However, traditional endoscopes provide better control during examinations, and over time, a complete operating procedure has been developed to ensure a relative completeness of examinations. In contrast, the capsule endoscope lacks somewhat a self-checking method for examination completeness.

For one thing, the capsule endoscope has poor controllability. Gastrointestinal peristalsis, capsule movement and other factors within the examination space result in random capture of images. Even when an external magnetic control device is used, it is difficult to guarantee a complete imaging of the examination space, that is, some parts may be missed. For another, due to the poor controllability and lack of feedback on capsule position and orientation, it is difficult to establish a good operating procedure to ensure examination completeness. Furthermore, the capsule endoscope lacks the capability to clean its camera lens, resulting in significantly lower image resolution compared to traditional endoscopes, which can lead to inconsistent image quality. All of these problems contribute to the potential lack of completeness in capsule endoscopy examinations.

SUMMARY OF THE INVENTION

In order to technically solve the above problems in the prior art, it is an object of the present invention to provide a completeness self-checking method of a capsule endoscope, an electronic device, and a readable storage medium.

In order to realize one of the above objects of the present invention, an embodiment of the present invention provides a completeness self-checking method of a capsule endoscope. The method comprises the steps of: establishing a virtual positioning area based on a working area of the capsule endoscope, where the virtual positioning area and the working area are located in the same spatial coordinate system, and the virtual positioning area entirely covers the working area;

- dividing the virtual positioning area into a plurality of adjacent voxels of the same size, where each voxel has a unique identifier and coordinates;
- driving the capsule endoscope to move within the working area, sequentially recording the images captured by the capsule endoscope when it reaches each working point at a predetermined frequency, and synchronously executing a step A to label the voxels with illuminated identifiers, where, the step A is no longer synchronously executed when the percentage of voxels labeled with illuminated identifiers in the virtual positioning area is not less than a predefined percentage threshold;
- where none of the voxels are labeled with illuminated identifiers in an initial state;
- where the step A comprises:
- sequentially recording the position and field of view orientation of each working point in the spatial coordinate system;
- determining at each working point an intersection area between the field of view of the capsule endoscope and the virtual positioning area based on the position and field of view orientation of current working point;
- obtaining each voxel that is not labeled with illuminated identifier in each intersection area, and obtaining a line of sight vector from the current working point to each voxel that is not labeled with illuminated identifier, and merging the line of sight vectors corresponding to each voxel into the same vector set in sequence according to the order in which the intersection areas are obtained;
- traversing the vector set, and if the number of any line of sight sector in the vector set is at least 2, and if there exists an intersection angle between two line of sight vectors greater than a preset angle threshold, labeling the voxels corresponding to the current vector set with illuminated identifiers.

In an embodiment of the present invention, "driving the capsule endoscope to move within the working area, sequentially recording the images captured by the capsule endoscope when it reaches each working point at a predetermined frequency, and synchronously executing a step A to label the voxels with illuminated identifiers" comprises:

- scoring the images captured at each working point, synchronously executing the step A if the score for the images captured at the current working point is not less than a preset score, and skipping the step A for the current working point if the score for the images captured at the current working point is less than the preset score.

In an embodiment of the present invention, when executing step A, the method further comprises:

- if the distance between two positioning points is less than a preset distance threshold, and the angle between the field of view orientations of the two positioning points is less than the preset angle threshold, then when traversing the vector sets intersecting within the field of view ranges of the current two positioning points, omitting a calculation of angles between the line of sight vectors corresponding to each voxel to the two positioning points within the field of view intersection range.

In an embodiment of the present invention, the method further comprises:

determining in real time whether the percentage of voxels that are labeled with illuminated identifiers within the virtual positioning area is not less than the predefined percentage threshold;

if the percentage of voxels is not less than the predefined percentage threshold, driving the capsule endoscope to exit the working mode;

if the percentage of voxels is less than the predefined percentage threshold, driving the capsule endoscope to continue the working mode.

In an embodiment of the present invention, the method further comprises:

determining whether the percentage of voxels that are labeled with illuminated identifiers within the virtual positioning area is not less than the predefined percentage threshold when the capsule endoscope runs for a preset duration within the working area;

if the percentage of voxels is not less than the predefined percentage threshold, driving the capsule endoscope to exit the working mode;

if the percentage of voxels is less than the predefined percentage threshold, driving the capsule endoscope to continue the working mode.

In an embodiment of the present invention, the virtual positioning area is configured as spherical.

In an embodiment of the present invention, the method further comprises: taking a coordinate value of center point of each voxel as a coordinate value of current voxel.

In an embodiment of the present invention, the preset angle threshold is configured as 90%;

the value range for the preset angle threshold is configured to belong to the set [60°, 120°];

each voxel is configured as a regular cube, with side length range belonging to the set [1 mm, 5 mm].

In order to realize one of the above objects of the present invention, an embodiment of the present invention provides an electronic device, comprising a memory and a processor. The memory stores a computer program that can run on the processor, and the processor executes the program to implement the steps of the completeness self-checking method of the capsule endoscope.

In order to realize one of the above objects of the present invention, an embodiment of the present invention provides a computer-readable storage medium for storing a computer program. The computer program is executed by the processor to implement the steps of the completeness self-checking method of the capsule endoscope.

The present invention has he following advantages compared with the prior art. The present invention provides the completeness self-checking method of the capsule endoscope, the electronic device, and the readable storage medium, which can, by establishing a virtual positioning area within the same spatial coordinate system as the working area, and labeling the voxels with illuminated identifiers in the virtual positioning area, achieve self-checking completeness of the capsule endoscope, and enhance the probability of detection.

DETAILED DESCRIPTION

The present invention can be described in detail below with reference to the accompanying drawings and preferred embodiments. However, the embodiments are not intended to limit the present invention, and the structural, method, or functional changes made by those skilled in the art in accordance with the embodiments are included in the scope of the present invention.

Figure 1:
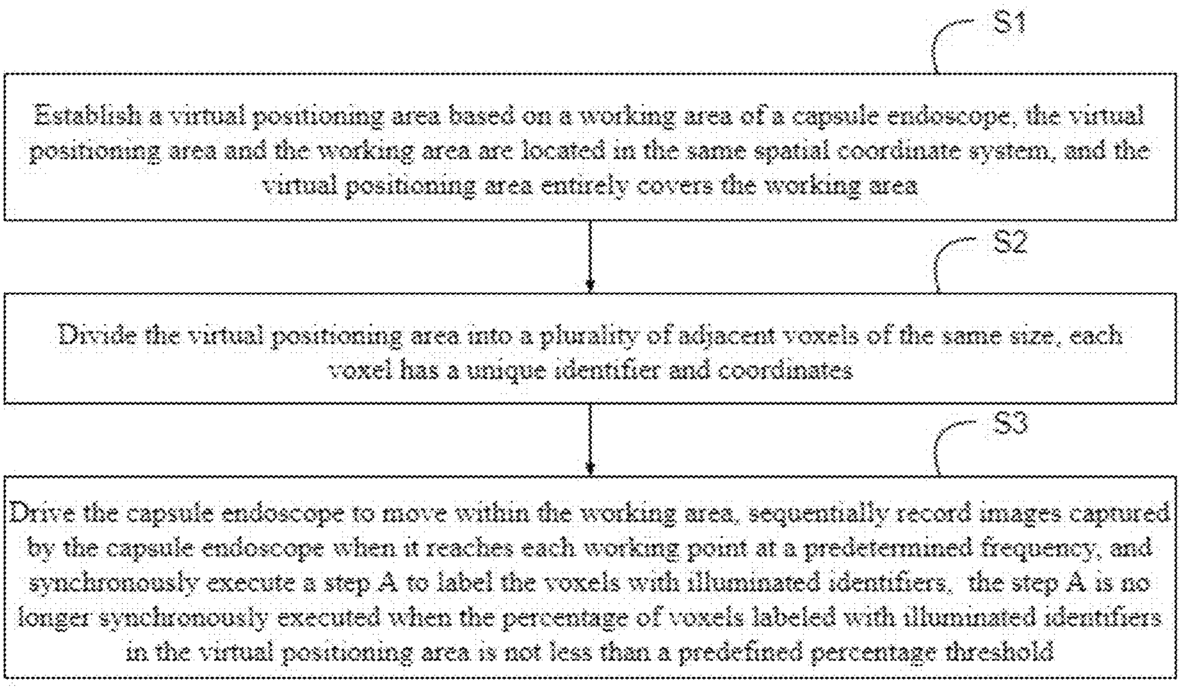
FIG. 1 is an exemplar process flow diagram of a completeness self-checking method of a capsule endoscope, in accordance with an embodiment of the present invention.
Figure 2:
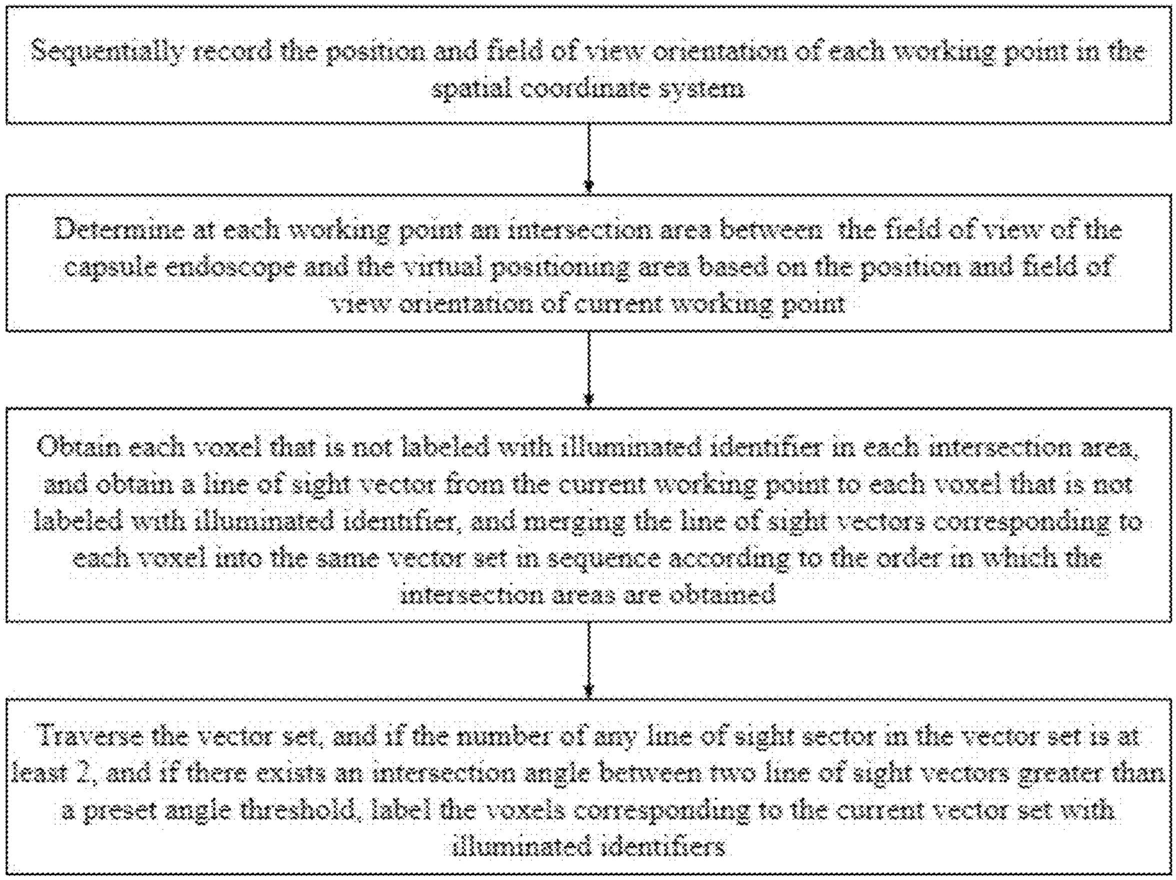
FIG. 2 is an exemplar process flow diagram of step A in FIG. 1.

Referring to FIG. 1 and FIG. 2, in a first embodiment, the present invention provides a completeness self-checking method of a capsule endoscope. The method comprises the following steps:

step S1, establishing a virtual positioning area based on a working area of the capsule endoscope, where the virtual positioning area and the working area are located in the same spatial coordinate system, and the virtual positioning area entirely covers the working area.

step S2, dividing the virtual positioning area into a plurality of adjacent voxels of the same size, where each voxel has a unique identifier and coordinates.

step S3, driving the capsule endoscope to move within the working area, sequentially recording images captured by the capsule endoscope when it reaches each working point at a predetermined frequency, and synchronously executing a step A to label the voxels with illuminated identifiers, where, the step A is no longer synchronously executed when the percentage of voxels labeled with illuminated identifiers in the virtual positioning area is not less than a predefined percentage threshold.

In an initial state, none of the voxels are labeled with illuminated identifiers.

The step A comprises the following specific steps:

sequentially recording the position and field of view orientation of each working point in the spatial coordinate system;

determining at each working point an intersection area between the field of view of the capsule endoscope and the virtual positioning area based on the position and field of view orientation of current working point;

obtaining each voxel that is not labeled with illuminated identifier in each intersection area, and obtaining a line of sight vector from the current working point to each voxel that is not labeled with illuminated identifier, and merging the line of sight vectors corresponding to each voxel into the same vector set in sequence according to the order in which the intersection areas are obtained;

traversing the vector set, and if the number of any line of sight sector in the vector set is at least 2, and if there exists an intersection angle between two line of sight vectors greater than a preset angle threshold, labeling the voxels corresponding to the current vector set with illuminated identifiers.

Figure 3:
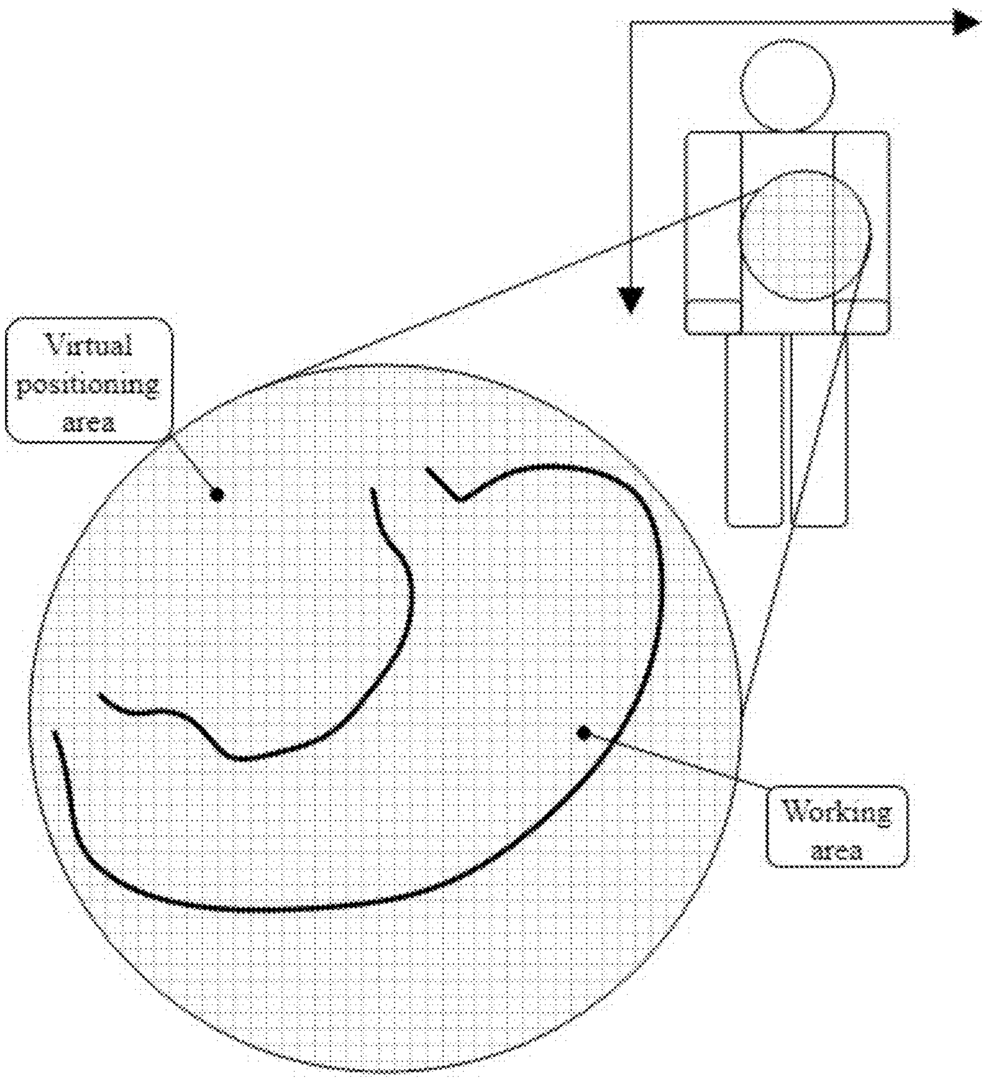
FIG. 3 is a structural schematic diagram of a specific example of the present invention.

Referring to FIG. 3, in an embodiment of the present invention, a virtual gastric environment is used as an example to provide a detailed introduction. Specifically, for step S1, the working area is typically a determined examination space. Therefore, after determining the working area, within the same spatial coordinate system as the working area, a virtual positioning area can be established based on prior art.

In an embodiment of the present invention, the virtual positioning area is configured as spherical. For the sake of clarity, FIG. 3 in the embodiment only illustrates one cross-section. Here, the virtual positioning area encompasses the entire stomach.

For step S2, the virtual positioning areas is discretized, dividing it into a plurality of adjacent voxels of the same size. In an embodiment of the present invention, each voxel is configured as a regular cube, with side length range belonging to the set [1 mm, 5 mm]. Accordingly, each voxel has a unique identifier and coordinates. The identifier is a number, for example. The coordinates may be a coordinate value of a fixed position of each voxel, for example: a coordinate value of one of an edge corner. In an embodiment of the present invention, the coordinate value of center point of each voxel is taken as the coordinate value of current voxel.

It can be understood that, in practical applications, a platform can be set, and after a user is within the monitoring area of the platform, the virtual positioning areas can be automatically constructed based on the position of the user, and the user remains within the monitoring area throughout the operation of the capsule endoscope, ensuring that the virtual positioning areas and the working area are located in the same spatial coordinate system.

For step S3, the capsule endoscope is driven into the working area, it records each working point at a predetermined frequency, and depending on specific requirements, it may selectively record images captured at each working point, the spatial coordinate value P(x, y, z), and the field of view orientation M of each working point. The field of view orientation here refers to the orientation of the capsule endoscope, which may be Euler angles (yaw, pitch, roll) for example, or quaternions, or vector coordinates of the orientation. Based on the field of view orientation, it can determine the field of view of the capsule endoscope capturing image in the orientation M at the current coordinate point. The field of view orientation forms a shape of a cone with the current coordinate point as a starting point, of which, the vector direction is $\overrightarrow{PM}$, that is the extension of the axis of the cone. Capturing images with the capsule endoscope, orienting its positioning coordinates, and recording the field of view orientation are all existing technology and will not be further described here.

In a preferred embodiment of the present invention, the step 3 further comprises: scoring the images captured at each working point, and synchronously executing the step A if the score for the images captured at the current working point is not less than a preset score, or skipping the step A for the current working point if the score for the images captured at the current working point is less than the preset score.

Scoring of images can be performed in various ways, which are prior art. For example, Chinese Patent Application with publication number CN111932532B, entitled "Referenceless image evaluation method for capsule endoscope, electronic device, and medium" is cited in the present application. US patent application U.S. Ser. No. 18/027,921, which takes priority from Chinese Patent Application CN111932532B, and U.S. patent application Ser. No. 18/027,921 is also cited in the present invention. The scoring in the present invention may be an image quality evaluation score, and/or an image content evaluation score, and/or a composite score, as mentioned in the cited patent. Further details are not provided here.

Preferably, when the capsule endoscope reaches each working point, step A is synchronously executed to label the voxels with illuminated identifiers, and when the percentage of voxels labeled with illuminated identifiers in the virtual positioning area is not less than the predefined percentage threshold, step A is no longer synchronously executed. The examination completeness of the capsule endoscope can be determined by the percentage of voxels labeled with illuminated identifiers. A higher percentage indicates a more complete examination of the working area by the capsule endoscope.

For step A, specifically, in an initial state, each voxel point is defaulted to not having an illuminated identifier. The illuminated identifier is a generic marking, and the marking process in step A can be achieved through various ways. For example, the corresponding voxel points can be identified using the same code or the same color. After specific calculations, different voxel points are sequentially illuminated, and then the examination progress of the working area can be determined through the percentage of voxels labeled with illuminated identifiers. Alternatively, in other embodiments of the present invention, it is also possible to start with all voxels illuminated in the initial state and sequentially turn off each voxel in the order of step A. Further details are not provided here.

Preferably, the preset angle threshold is a set angle value, which can be adjusted as needed. In an embodiment of the present invention, the value range for the preset angle threshold is configured to belong to the set [60°, 120°].

Figure 4:
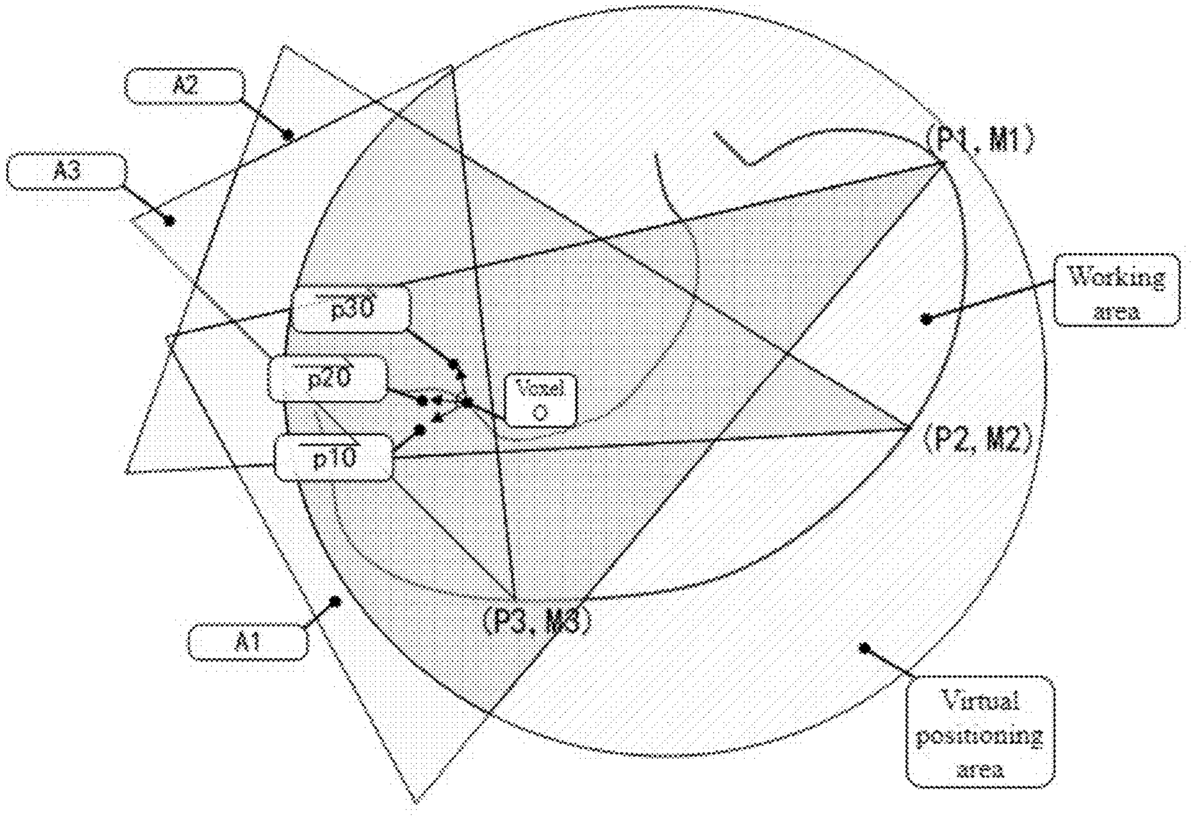
FIG. 4 is a structural schematic diagram of another example of the present invention.
Figure 5:
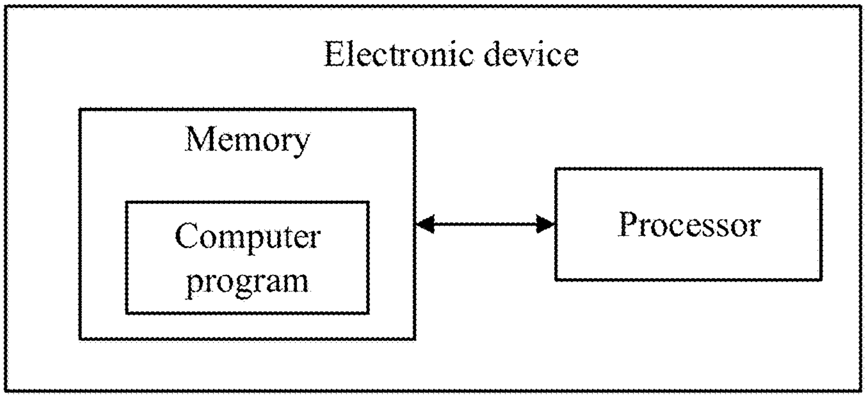
FIG. 5 is a schematic illustration of an embodiment of the present invention.

Referring to FIG. 4, in step A, for each working point, its cone-shaped area can be calculated based on its corresponding field of view orientation. Accordingly, the cone-shaped area and the spherical virtual positioning area have an intersection area. Using coordinate point P1 as an example, its intersection area is denoted as A1. The voxel O is one of the voxel points in the intersection area A1.

Taking voxel point O as an example, the line of sight vector between the coordinate point P1 and the voxel point O is $\overrightarrow{p1o}$, i.e., the vector pointing from P1 to O.

Further, when the capsule endoscope moves to the coordinate point P2, an intersection area A2 is formed between the field of view of the capsule endoscope and the virtual positioning area. Continuing with voxel point O as an example, the line of sight vector between the coordinate point P2 and the voxel point O is $\overrightarrow{p2o}$. For voxel O, its vector set contains 2 line of sight vectors, namely $\overrightarrow{p1o}$ and $\overrightarrow{p2o}$. At this point, it is necessary to calculate the intersection angle between the two line of sight vectors corresponding to voxel O. After performing the calculation, the obtained intersection angle between them is 30°. Assuming that the preset angle threshold is 90°, since the obtained intersection angle of 30° is less than the preset angle threshold of 90°, the vector set corresponding to the voxel point O is retained, and monitoring continues.

When the capsule endoscope moves to the coordinate point P3, an intersection area A3 is formed between the field of view of the capsule endoscope and the virtual positioning area. Continuing with the voxel point O as an example, the line of sight vector between the coordinate point P3 and the voxel point O is $\overrightarrow{p3o}$. At this point, for voxel O, its vector set contains 3 line of sight vectors, namely $\overrightarrow{p1o}$, $\overrightarrow{p2o}$ and $\overrightarrow{p3o}$.

Then, it is necessary to calculate the intersection angle between any two line of sight vectors corresponding to voxel O. After performing the calculation, the obtained intersection angle between $\overrightarrow{p1o}$ and $\overrightarrow{p3o}$ is 100°. Assuming that the preset angle threshold is 90°, since the obtained intersection angle of 100° is greater than the preset angle threshold of 90°, the voxel point O is labeled with an illuminated identifier.

When the capsule endoscope moves to the next coordinate point, its corresponding intersection area may still cover voxel O. However, since voxel O has already been labeled with an illuminated identifier, it is not recalculated.

As per the operations in the above step A, each voxel point within the virtual positioning area can be labeled with illuminated identifiers sequentially. Ideally, when the capsule endoscope completes its work, every voxel point in the virtual positioning area should be illuminated. However, in practical operations, various interfering factors can introduce errors. Therefore, the present invention provides a predefined percentage threshold. When the percentage of voxels that are labeled with illuminated identifiers within the virtual positioning area is not less than the predefined percentage threshold, it indicates that the capsule endoscope's monitoring range meets the standard. In this way, the illumination of voxels within the virtual positioning area is used to assist in the completeness self-check of the capsule endoscope.

Further, the examination results are visualized, allowing users to verify the examination area of the capsule endoscope by observing the illuminated identifiers within the virtual positioning area. Additional details are not provided here.

Since the working area is typically irregular in shape, and more specifically, it is typically not a convex curved surface in its entirety, that is, some areas may be blocked, a certain voxel is covered in the field of view of a working point, but actually it is not sure to be captured. So, for the voxel O in the example, it is not actually visible in the fields of view of coordinate points P1 and P2. But in the present invention, the voxels are observed from multiple angles and are only labeled with illuminated identifiers when the intersection angle between the respective line of sight vectors is greater than the preset angle threshold. Therefore, it significantly improves the accuracy of the calculation probability.

Preferably, when executing step A, the method further comprises:

- if the distance between two positioning points is less than a preset distance threshold, and the angle between the field of view orientations of the two positioning points is less than the preset angle threshold, then when traversing the vector sets intersecting within the field of view ranges of the current two positioning points, omitting a calculation of angles between the line of sight vectors corresponding to each voxel to the two positioning points within the field of view intersection range. When the deviation between two positioning points is small, their intersection areas may approximately coincide, and at this point, it is highly unlikely that voxel points within their intersection areas are labeled with illuminated identifiers. Therefore, by adding this step, it is possible to reduce calculation workload while ensuring the accuracy of the calculation results.

In most cases, the two positioning points mentioned here are typically two coordinate points obtained sequentially within the same examination area. Further details are not provided here.

Preferably, the method further comprises: determining in real time whether percentage of voxels that are labeled with illuminated identifiers within the virtual positioning area is not less than the predefined percentage threshold, if the percentage of voxels is not less than the predefined percentage threshold, driving the capsule endoscope to exit the working mode; if the percentage of voxels is less than the predefined percentage threshold, driving the capsule endoscope to continue the working mode.

Preferably, the method further comprises: determining whether the percentage of voxels that are labeled with illuminated identifiers within the virtual positioning area is not less than the predefined percentage threshold when the capsule endoscope runs for a preset duration within the working area, if the percentage is not less than the predefined percentage threshold, driving the capsule endoscope to exit the working mode; if the percentage is less than the predefined percentage threshold, driving the capsule endoscope to continue the working mode.

Using the percentage of voxels that are labeled with illuminated identifiers within the virtual positioning area to determine whether to end the working mode allows for multi-angle observation of the working area. This approach enables an increase in the number of images taken from different angles within the same area, ensuring comprehensive coverage. It also provides the advantage of better observation and higher detection rates when analyzing images in post-processing applications.

Further, the present invention provides an electronic device, comprising a memory and a processor. The memory stores a computer program that can run on the processor, and the processor executes the program to implement the steps of the completeness self-checking method of the capsule endoscope.

Further, the present invention provides a computer-readable storage medium for storing a computer program. The computer program is executed by the processor to implement the steps of the completeness self-checking method of the capsule endoscope.

In summary, the present invention provides the completeness self-checking method of the capsule endoscope, the electronic device, and the readable storage medium, which can, by establishing a virtual positioning area within the same spatial coordinate system as the working area, and labeling the voxels with illuminated identifiers in the virtual positioning area, achieve self-checking completeness of the capsule endoscope, and additionally, enable visualization of the examination results, and enhance the convenience of operating the capsule endoscope.

It should be understood that, although the description is described in terms of embodiments, not every embodiment merely comprises an independent technical solution. Those skilled in the art should have the description as a whole, and the technical solutions in each embodiment may also be combined as appropriate to form other embodiments that can be understood by those skilled in the art.

The series of detailed descriptions set forth above are only specific descriptions of feasible embodiments of the present invention and are not intended to limit the scope of protection of the present invention. On the contrary, many modifications and variations are possible within the scope of the appended claims.

The invention claimed is:

1. A completeness self-checking method of a capsule endoscope, comprising:

- establishing a virtual positioning area based on a working area of the capsule endoscope, wherein the virtual positioning area and the working area are located in the same spatial coordinate system, and the virtual positioning area entirely covers the working area;

dividing the virtual positioning area into a plurality of adjacent voxels of the same size, wherein each voxel has a unique identifier and coordinates;

driving the capsule endoscope to move within the working area, sequentially recording the images captured by the capsule endoscope when it reaches each working point at a predetermined frequency, and synchronously executing a step A to label the voxels with illuminated identifiers, upon determining none of the voxels are labeled with the illuminated identifiers in an initial state;

not synchronously executing the step A upon determining the percentage of voxels labeled with the illuminated identifiers in the virtual positioning area is not less than a predefined percentage threshold;

wherein the step A comprises:

sequentially recording the position and field of view orientation of the capsule endoscope at each working point in the spatial coordinate system;

determining, for the capsule endoscope, at each working point an intersection area between the field of view of the capsule endoscope and the virtual positioning area based on the position and field of view orientation of the capsule endoscope at the current working point;

obtaining each voxel that is not labeled with the illuminated identifier in each intersection area, and obtaining a line of sight vector, for the capsule endoscope, from the current working point to each voxel that is not labeled with the illuminated identifier, and merging the line of sight vectors corresponding to each voxel into the same vector set in sequence according to the order in which the intersection areas are obtained;

traversing the vector set, and if the number of any line of sight vector in the vector set is at least 2, and if there exists an intersection angle between two line of sight vectors, of the capsule endoscope at the working points, greater than a preset angle threshold, labeling the voxels corresponding to the current vector set with the illuminated identifiers.

2. The method of claim 1, wherein the step of driving the capsule endoscope to move within the working area, sequentially recording the images captured by the capsule endoscope when it reaches each working point at the predetermined frequency, and synchronously executing a step A to label the voxels with the illuminated identifiers comprises:

scoring the images captured at each working point, synchronously executing the step A if the score for the images captured at the current working point is not less than a preset score, and skipping the step A for the current working point if the score for the images captured at the current working point is less than the preset score.

3. The method of claim 1, wherein, when executing step A, the method further comprises:

if the distance between two positioning points is less than a preset distance threshold, and the angle between the field of view orientations of the two positioning points is less than the preset angle threshold, then when traversing the vector sets intersecting within the field of view ranges of the current two positioning points, omitting a calculation of angles between the line of sight vectors corresponding to each voxel to the two positioning points within the field of view intersection range.

4. The method of claim 1, wherein the method further comprises:

determining in real time whether the percentage of voxels that are labeled with the illuminated identifiers within the virtual positioning area is not less than the predefined percentage threshold;

if the percentage of voxels is not less than the predefined percentage threshold, driving the capsule endoscope to exit the working mode;

if the percentage of voxels is less than the predefined percentage threshold, driving the capsule endoscope to continue the working mode.

5. The method of claim 1, wherein the method further comprises:

determining whether the percentage of voxels that are labeled with the illuminated identifiers within the virtual positioning area is not less than the predefined percentage threshold when the capsule endoscope runs for a preset duration within the working area;

if the percentage of voxels is not less than the predefined percentage threshold, driving the capsule endoscope to exit the working mode;

if the percentage of voxels is less than the predefined percentage threshold, driving the capsule endoscope to continue the working mode.

6. The method of claim 1, wherein the virtual positioning area is configured as spherical.

7. The method of claim 1, wherein the method further comprises: taking a coordinate value of center point of each voxel as a coordinate value of current voxel.

8. The method of claim 1, wherein the preset angle threshold is configured as 90%;

the value range for the preset angle threshold is configured to belong to the set [60°, 120°];

each voxel is configured as a regular cube, with side length range belonging to the set [1 mm, 5 mm].

9. An electronic device, comprising a memory and a processor, wherein the memory stores a computer program that runs on the processor, and the processor executes the program to implement steps of a completeness self-checking method of a capsule endoscope, wherein the method comprises:

establishing a virtual positioning area based on a working area of the capsule endoscope, wherein the virtual positioning area and the working area are located in the same spatial coordinate system, and the virtual positioning area entirely covers the working area;

dividing the virtual positioning area into a plurality of adjacent voxels of the same size, wherein each voxel has a unique identifier and coordinates;

driving the capsule endoscope to move within the working area, sequentially recording the images captured by the capsule endoscope when it reaches each working point at a predetermined frequency, and synchronously executing a step A to label the voxels with illuminated identifiers, wherein, the step A is no longer synchronously executed when the percentage of voxels labeled with the illuminated identifiers in the virtual positioning area is not less than a predefined percentage threshold;

wherein none of the voxels are labeled with the illuminated identifiers in an initial state;

wherein the step A comprises:

sequentially recording the position and field of view orientation, of the capsule endoscope, at each working point in the spatial coordinate system;

determining at each working point an intersection area between the field of view of the capsule endoscope and the virtual positioning area based on the position and field of view orientation of the capsule endoscope at the current working point;

obtaining each voxel that is not labeled with the illuminated identifier in each intersection area, and obtaining a line of sight vector from the current working point to each voxel that is not labeled with the illuminated identifier, and merging the line of sight vectors corresponding to each voxel into the same vector set in sequence according to the order in which the intersection areas are obtained;

traversing the vector set, and if the number of any line of sight vector in the vector set is at least 2, and if there exists an intersection angle between two line of sight vectors greater than a preset angle threshold, labeling the voxels corresponding to the current vector set with the illuminated identifiers.

10. A computer-readable storage medium having stored thereon a computer program that, when executed by a processor, implements steps of a completeness self-checking method of a capsule endoscope, wherein the method comprises:

establishing a virtual positioning area based on a working area of the capsule endoscope, wherein the virtual positioning area and the working area are located in the same spatial coordinate system, and the virtual positioning area entirely covers the working area;

dividing the virtual positioning area into a plurality of adjacent voxels of the same size, wherein each voxel has a unique identifier and coordinates;

driving the capsule endoscope to move within the working area, sequentially recording the images captured by the capsule endoscope when it reaches each working point at a predetermined frequency, and synchronously executing a step A to label the voxels with illuminated identifiers, wherein, the step A is no longer synchronously executed when the percentage of voxels labeled with the illuminated identifiers in the virtual positioning area is not less than a predefined percentage threshold;

wherein none of the voxels are labeled with the illuminated identifiers in an initial state;

wherein the step A comprises:

sequentially recording the position and field of view orientation of the capsule endoscope at each working point in the spatial coordinate system;

determining at each working point an intersection area between the field of view of the capsule endoscope and the virtual positioning area based on the position and field of view orientation of the current working point;

obtaining each voxel that is not labeled with the illuminated identifier in each intersection area, and obtaining a line of sight vector from the current working point to each voxel that is not labeled with the illuminated identifier, and merging the line of sight vectors corresponding to each voxel into the same vector set in sequence according to the order in which the intersection areas are obtained;

traversing the vector set, and if the number of any line of sight vector in the vector set is at least 2, and if there exists an intersection angle between two line of sight vectors greater than a preset angle threshold, labeling the voxels corresponding to the current vector set with the illuminated identifiers.

* * * * *